US007566337B2

(12) United States Patent
Søgaard-Andersen et al.

(10) Patent No.: US 7,566,337 B2
(45) Date of Patent: *Jul. 28, 2009

(54) METHOD FOR PREVENTION OF A PARASTOMAL HERNIA IN A PATIENT

(75) Inventors: Torben Søgaard-Andersen, Draguignan (FR); Ismail Gögenur, Greve (DK); Anders Fischer, Charlottenlund (DK)

(73) Assignee: Nortec Medical Development S.A., Luxembourg (LU)

( * ) Notice: Subject to any disclaimer, the term of this patent is extended or adjusted under 35 U.S.C. 154(b) by 330 days.

This patent is subject to a terminal disclaimer.

(21) Appl. No.: 11/454,377

(22) Filed: Jun. 15, 2006

(65) Prior Publication Data

US 2006/0276908 A1  Dec. 7, 2006

Related U.S. Application Data

(63) Continuation-in-part of application No. 10/537,713, filed as application No. PCT/IB03/02889 on Jul. 21, 2003.

(30) Foreign Application Priority Data

Jul. 25, 2002 (DK) ............................... 2002 01137
Sep. 18, 2002 (DK) ............................... 2002 01376

(51) Int. Cl.
*A61B 17/08* (2006.01)
*A61F 2/02* (2006.01)
(52) U.S. Cl. ..................................... 606/151; 623/23.72
(58) Field of Classification Search ... 623/23.64–23.67; 606/151
See application file for complete search history.

(56) References Cited

U.S. PATENT DOCUMENTS

| 5,098,397 | A | 3/1992 | Svensson et al. ............. 604/175 |
| 5,098,398 | A | 3/1992 | Lundgren .................... 604/175 |
| 6,017,355 | A | 1/2000 | Hessel et al. ................. 606/184 |
| 6,425,924 | B1 * | 7/2002 | Rousseau .................. 623/23.64 |
| 6,669,735 | B1 * | 12/2003 | Pelissier ................... 623/23.74 |
| 6,726,660 | B2 * | 4/2004 | Hessel et al. ................. 604/175 |

FOREIGN PATENT DOCUMENTS

| WO | WO 87/06122 | 10/1987 | |
| WO | WO 01/08597 | 2/2001 | |
| WO | WO 2004/010897 A1 | 2/2004 | .................. 604/338 |

* cited by examiner

*Primary Examiner*—Suzette J Gherbi
(74) *Attorney, Agent, or Firm*—Winston & Strawn LLP (57) ABSTRACT

A method for prevention of a parastomal hernia in a patient. First and second incisions are made in the skin, with the second incision made in the external rectus fascia above the first incision. An implant of a substantially flat ring having a central opening and provided with a number of anchoring elements radiating from an outer circumference of the ring is introduced through the first incision. The central opening of the implant is arranged above the second incision, and the anchoring elements are directed to securing positions on top of the fascia. Next an end of an intestine is pulled through the second incision, the central opening of the implant, and the first incision, to create the stoma. The anchoring elements serve to keep the implant fixated and secured to the fascia while exerting pressure on the muscles to thereby reinforce the muscle structure and prevent hernia formation.

11 Claims, 5 Drawing Sheets

METHOD FOR PREVENTION OF A PARASTOMAL HERNIA IN A PATIENT

CROSS-REFERENCE TO RELATED APPLICATIONS

This application is a continuation-in-part of application Ser. No. 10/537,713 filed Jun. 3, 2005, which is the US national phase of International application PCT/IB03/02889 filed Jul. 21, 2003, the entire content of each of which is expressly incorporated herein by reference.

BACKGROUND ART

The invention relates to a method for prevention of a parastomal hernia in a patient.

Incisional hernias can be a significant problem after open abdominal surgery. As an example parastomal hernia is a common complication after the construction of enterostomas with a rate of more than 30% in general surgical practice. Bringing out the enterostomy through a laparotomy wound has been disastrous in terms of infection, wound dehiscence and herniation. [Y. Cengiz and L. A. Israelsson, *Parastomal Hernia*, European Surg., Vol. 35 p. 28-31, February 2003].

Bringing out the stoma through the rectus abdominis muscle has been associated with a lower rate of parastomal hernia. After repair of parastomal hernia, the lowest rates of recurrence have been achieved with methods using a prosthetic mesh in a sublay technique [Petersen S., Henke G., Zimmerman L., Aumann G., Hellmich G., and Ludwig K., *Ventral Rectus Fascia Closure on Top of Mesh Hernia Repair in the Sublay Technique*; Plast Reconstr., Surg. 2004December; 114(7):1754-60].

The best measure would be to prevent the formation of a parastomal hernia [Israelsson L A., *Preventing and Treating Parastomal Hernia*, World J Surg 2005; 29: 1086-9]. This principle has been reported and the first randomised clinical trial in this field was by Janes et al. [Janes A., Cengiz Y., Israelsson L A., *Preventing parastomal hernia with a prosthetic mesh*., Arch Surg 2004, 139:1356-8; Janes A., Cengiz Y., Israelsson L A., *Randomized clinical trial of the use of a prosthetic mesh to prevent parastomal hernia*., Br J Surg 2004; 91:280-2]. Janes et al. found a prophylactic effect of incorporation of a sublay light weight mesh placed at the operation where the ostomy is performed.

Despite these disclosures, there is a need for improved treatment of hernias

SUMMARY OF THE INVENTION

The present invention now provides a novel method for prevention of a parastomal hernia in a patient. The novel and unique method according to the present invention whereby this is achieved comprises the steps of making a first incision in the skin, introducing through the first incision an implant comprising a substantially flat ring having a central opening, wherein the implant is provided with a number of anchoring means radiating from an outer circumference of the ring, positioning the opening of the ring substantially below the first incision on top of the external rectus fascia, directing the number of anchoring means to each their securing positions on top the fascia and securing the anchoring means to the fascia, making a second incision in the external rectus fascia, pulling an end of an intestine to be externalised through the second incision, the central opening of the implant, and the first incision, and creating the stoma.

The invention also relates to an apparatus for prevention of a parastomal hernia in a patient comprising an implant comprising a substantially flat ring having a central opening, wherein the implant is provided with a number of anchoring means radiating from an outer circumference of the ring, the opening of the ring configured and dimensioned to be positionable on top of the external rectus fascia of the patient, with the number of anchoring means configured and dimensioned to be securable to the fascia for holding the implant in position on top of the fascia, so that an end of an intestine of the patient can be received in the central opening of the implant to create a stoma.

The implant effectively retains and guides the intestine in an area of the abdominal cavity in risk of hernia formations to prevent such hernia formations. The flexibility of the implant furthermore means that the patient cannot feel it in its implanted state.

Suitable substantially two-dimensionally implants are described in the applicant's International patent application no. WO 2004/010897. These implants are incorporated by reference in the present application. Suitable implants include implants comprising a flat ring, having an inner ring diameter and an outer ring diameter, and at least one elongated anchoring means radiating from the exterior circumference of the ring to a free end. The anchoring means serve for anchoring the implant and secure it on the prefixed implantation site on top of the external rectus fascia.

Both the implant and the anchoring means can expediently be made of a biocompatible material to ensure that the implant will not provoke irritation or inflammation at the risk of rejection. The material chosen for the anchoring means must furthermore be flexible so that the anchoring means easily can be directed in direction towards their anchoring site. An implant designed in the above way as a mainly flat ring will not take up much space in the abdominal cavity, into which it is implanted, and will therefore not be felt by the patient The anchoring means of the implant may be introduced one at a time in e.g. a laparotomy procedure through the first incision or the entire implant may be folded together and introduced through the first incision in one single step and allowed to reshape or unfold. After complete introduction of the implant the central opening of the implant is located above the second incision and each of the number of anchoring means is directed to each their anchoring position on top of the fascia by e.g. pulling a free end of each anchoring means through a corresponding third incisions in the skin. Subsequently the implant and/or the anchoring means are secured by e.g. sutures to the external rectus fascia.

Alternatively the number of anchoring means is directed to their securing positions on top of the fascia by mechanically straightening out the anchoring means in the space between the fascia and the skin. No third incisions are required in this alternative securing step. The surgeon simply manipulates the flexible, foldable and bendable anchoring means each at a time inside the body beneath the skin and above the fascia so that each anchoring means are straightened out to radiate from the ring.

The end of-the intestine, which is to be externalised, is first pulled through the second incision, secondly through the central opening of the implant and thirdly through the first incision. Finally, the stoma is created using surgical procedures known to the person skilled in the art.

In contrast to prior art methods in which hernia preventing meshes sublay the external rectus fascia, the implant onlay the external rectus fascia in the method according to the present invention.

Due to the procedure with placement of the implant in an onlay position, through a separate incision, the method is independent of the primary operation being performed by laparotomy or laparoscopy. Tumor resection is an example of a primary operation which often involves a secondary operation in which a stoma is made.

A suitable first incision are much smaller than the unfolded overall width of the implant. E.g. the width of the first incision is between ½-2 cm and the overall width of the implant is about 12 cm for a colostomy. A suitable second incision is made according to accommodation of the external diameter of the intestine to be externalised.

Anchoring means in form of e.g. lightweight PROLENE meshes are for example known from the inventor's own international patent application WO 01/08597. The length of the anchoring means can be adapted to the actual anatomic conditions, and the free end can in a simple way be secured in the adjacent fascia with for example knot sutures or staples.

The implant and the anchoring meshes can be made of any non-absorbable, non-degradeable, biocompatible, flexible material known in the art. Preferred materials are those that conventionally are used in the art for hernia treatment.

In the most preferred embodiment of the implant for use in the method according to the present invention the anchoring means are embedded in or is integrated with the ring. The preferred implant is one single integrated part laser-cut from a lightweight flexible material, such as an open-structured PROLENE mesh material. Some of these materials have a memory, that at least partly will contribute to restoration of the shape op the implant after introduction. This embodiment is especially inexpensive and quick to manufacture as the entire implant including the anchoring means can be made in one and the same processing step, for example at moulding or cutting from a larger workpiece.

Preferably, the serosa of the intestine is not fixated to the implant. Hence, any friction between the surface of the anchoring means and the fascia, and between the ring and the wall of the intestine passing through the ring can advantageously be avoided. Such friction can for example be generated by stress and tension caused by peristaltic movements of the intestine or mass movements, and repeated friction would at worst result in the injury of the intestine and its content seeping into and infecting the abdominal cavity.

To reduce the risk of infection and inflamation the implant can be imbedded in an antibiotic such as GENTAMYCIN® prior to implantation.

Another alternative way of reducing these risks is to use an implant provided with anchoring means which are distanced from the implant and thereby the intestine by means of at least one thread secured in the central opening of the implant and connected to the anchoring means at the anchoring end of this means. The threads are preferably made of a biocompatible material which is impregnated in a known way with an antimicrobial preparation such as $AgNO_3$ or an antibiotic to reduce the infection risk during and after implantation.

The thickness of the ring walls and the diameter of the rings can be the same or not and will typically depend on the specific application. Correspondingly, the anchoring means can be provided with different lengths. During the surgical procedure the length can be shortened to fit the anatomical conditions at the surgical site.

Within the scope of the present invention the surgeon may according to the circumstances and patients anatomy choose to modify the method so that the step of making a second incision is made subsequent to the step of making a first incision.

BRIEF DESCRIPTION OF THE DRAWINGS

The invention will be explained in greater details below, describing only exemplary embodiments with reference to the drawing, in which.

DETAILED DESCRIPTION OF THE PREFERRED EMBODIMENTS

Figure 1:
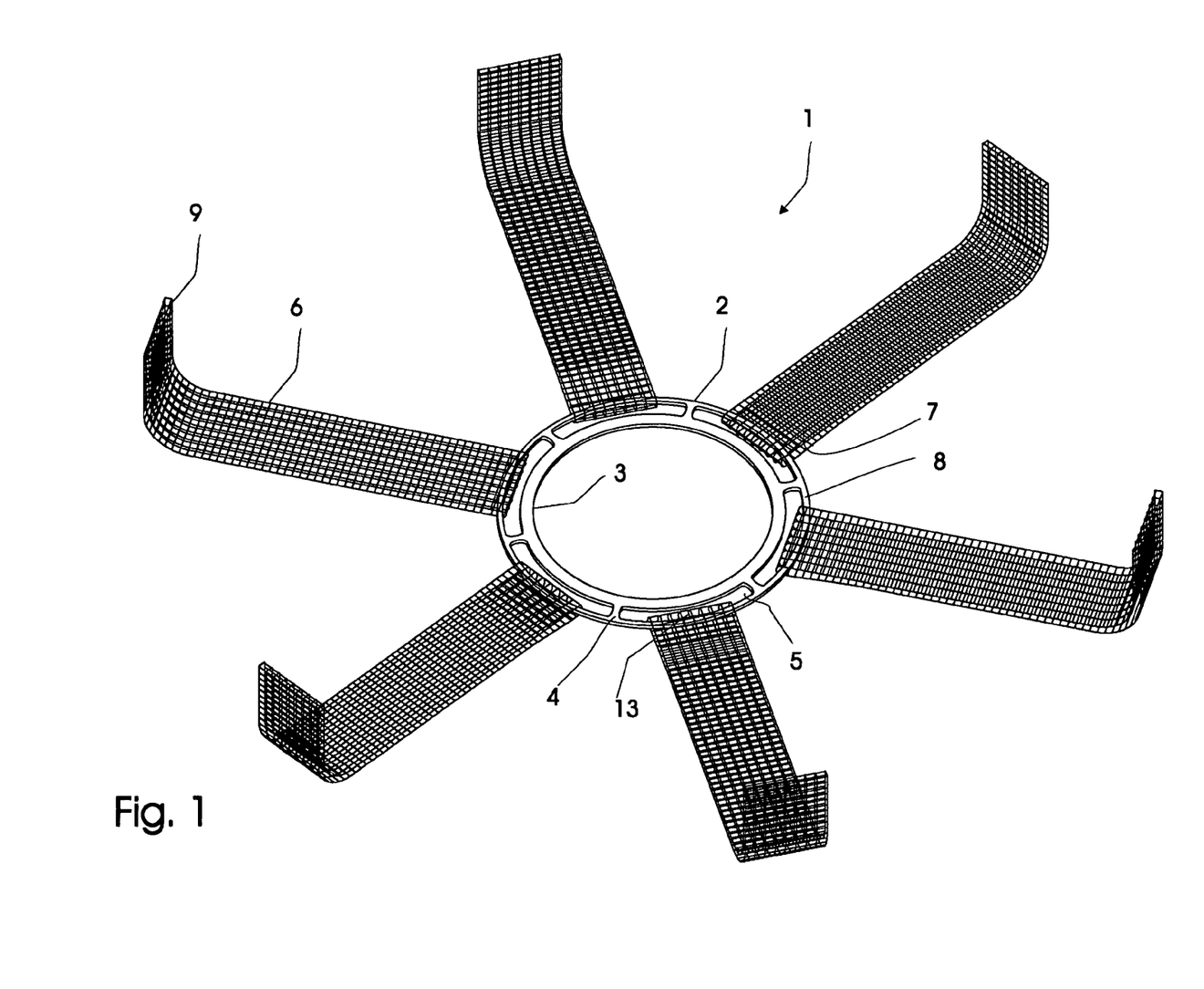
FIG. 1 is a perspective view of a first embodiment of an implant for use in the method according to the invention.

FIG. 1 is a perspective view of a implant 1 according to the invention. The implant 1 has an outer ring 2 and an inner ring 3. The outer ring 2 is connected to the inner ring 3 by means of, in this case, a total number of six connecting link 4. A connecting link 4 extends mainly perpendicularly from the radial inside face of the outer ring in an angle of 180° perpendicularly in on the radial outside face of the inner ring. The two rings are at a radial distance from each other arranged concentrically about their joint axis.

The connecting links 4 are located at equal angular distance from each other and form a total number of six openings 5 between the outer ring 2 and the inner ring 3. In each opening 5 an elongated mesh 6 is secured for on implantation anchoring the implant 1 in the external rectus fascia (not shown). The mesh 6 is secured around the section 8 of the outer ring 2 that forms part of an opening 5 by means of an anchoring end 7 and is extending to a free end 9 that is fixed to the external rectus fascia by means of e.g. sutures or staples (not shown).

Figure 2:
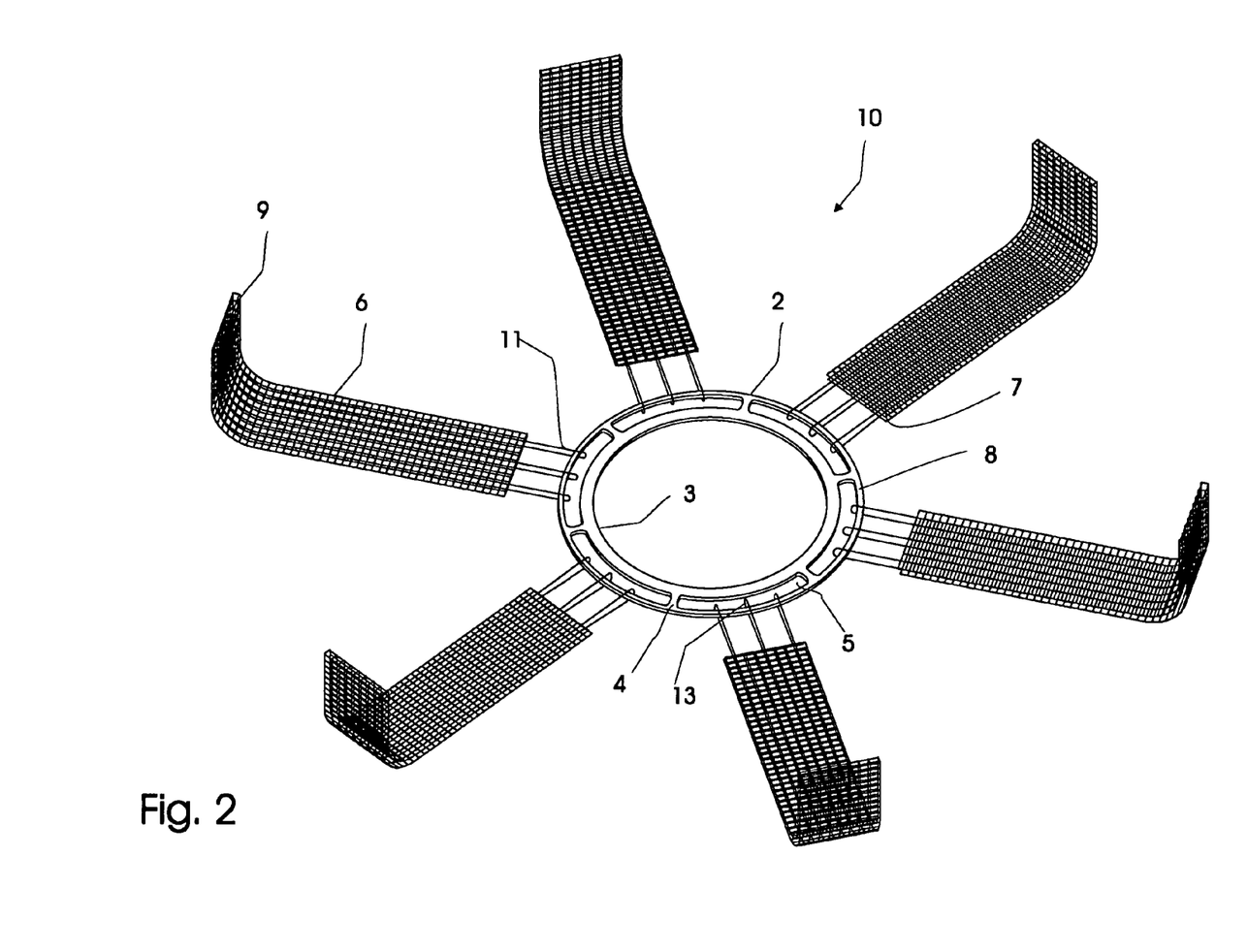
FIG. 2 is a perspective view of a second embodiment of an implant for use in the method according to the invention.
Figure 3:
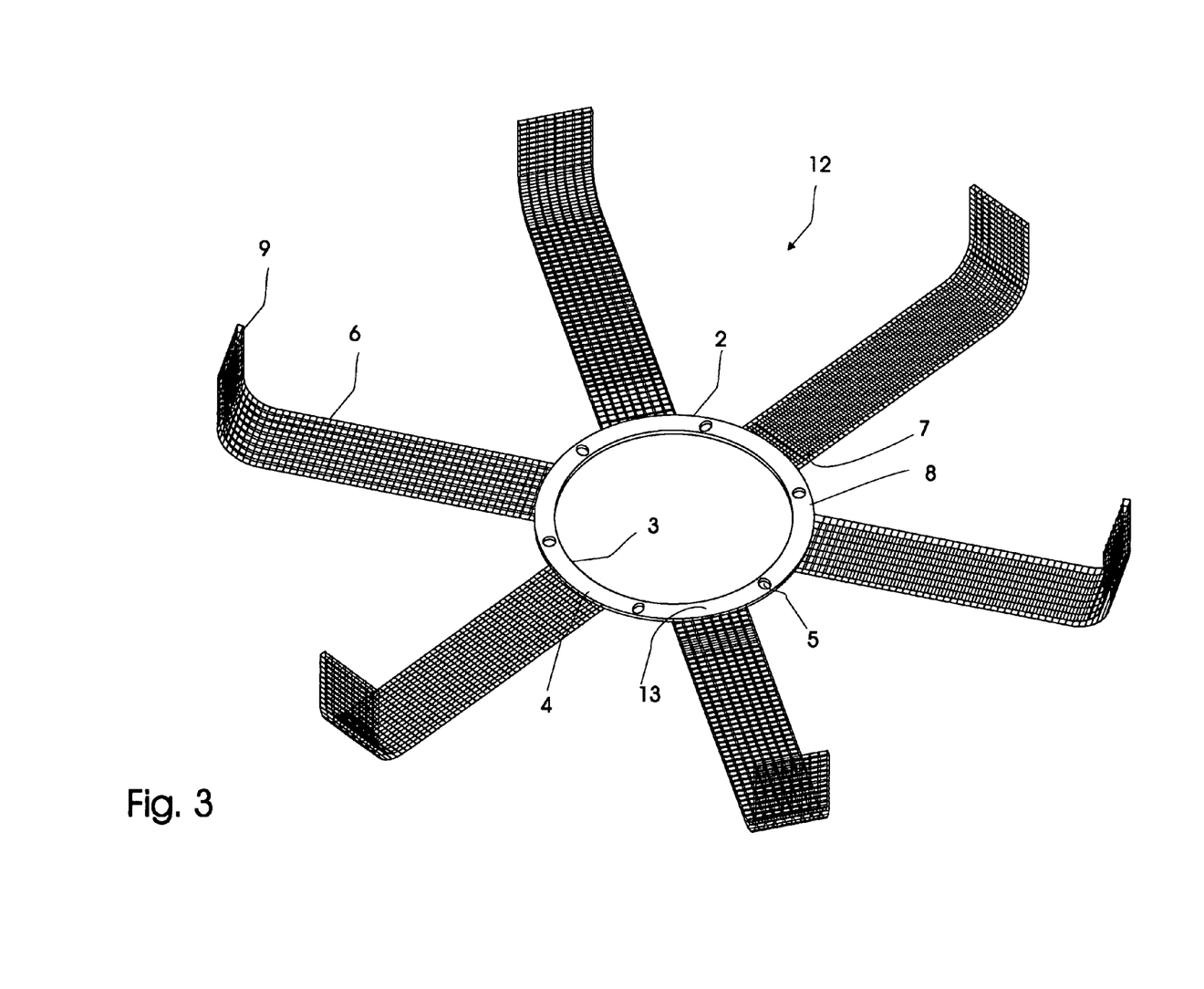
FIG. 3 is a perspective view of a third embodiment of an implant for use in the method according to the invention.

FIGS. 2 and 3 are modifications of the implant in FIG. 1 and like parts are similarly referenced.

In the embodiment 10 in FIG. 2 the mesh 6 is secured in the opening 5 via threads 11 extending from the anchoring end 7 of the mesh 6 to the section 8 of the outer ring 2 that forms part of an opening 5 for distancing the mesh from the inner ring.

FIG. 3 shows third embodiment 12 of an implant for use in the method according to the invention. The connecting links 4 connecting the outer ring 2 and the inner ring 3 are in this embodiment so wide that the anchoring part 7 of the mesh 6 can be embedded in at least the section 13 of the outer ring 2 in which a connecting link 4 ends. The openings 5 are also in this embodiment used for suturing the implant in a hypodermal area, and the meshes 6 are secured to the external rectus fascia on the way described above.

Figure 4:
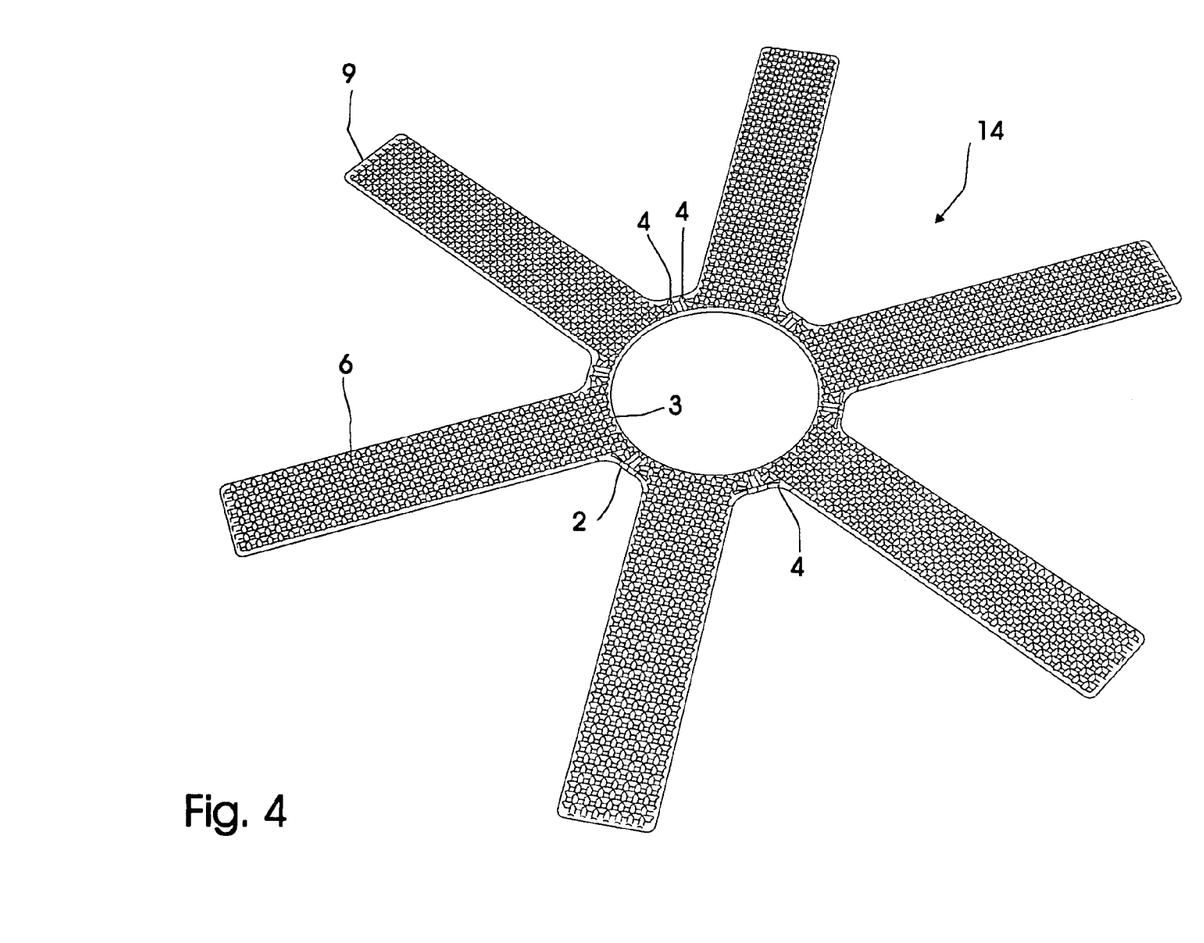
FIG. 4 is a perspective view of a fourth embodiment of an implant for use in the method according to the invention.

FIG. 4 shows a preferred fourth embodiment of the present invention, and like parts are similarly referenced. As the previous embodiments, the fourth embodiment of an implant 14 has an inner ring 3 and an outer ring 2. The embodiment of FIG. 4 differs from the others by the fact that both rings 2,3 only have a very small radial and axial extent, the rings preferably being designed as threads interconnected along the outer and inner periphery respectively of the rings via a number of similarly thread-shaped connecting links 4. These connecting links form a number of openings 5 or meshes between the two rings 2,3 so that the two rings appear as a flat, annular mesh from which a number of anchoring means are extending in form of radiating meshes 6. The preferred technique for producing the fourth embodiment of an implant 14 is to stamp or cut the implant from a sheet of mesh material. The distance between the inner diameter and the outer diameter of the ring, said ring includes the inner ring 3, the outer ring 2 and the material connecting these two rings 2,3, may vary between e.g ½ cm-2 cm. However the surgeon may select an implant of any appropriate dimension and extension depending on the patient, anatomy and condition.

The meshes of the implant 14, of which a total number of six are shown in this case, are extending from the inner ring 3 via the outer ring 2, which is incorporated in the mesh 6 towards its free end 9. Within the scope of the invention implants can be used with any kind of expedient number and lengths of anchoring means. Because the implant 14 is made of a flexible, and optionally more or less elastic, biocompatible material, the many small apertures, openings or meshes between the rings and in the meshes respectively advantageously can receive a suture or staple when the implant is in its implanted state. The implant is in this embodiment made of a continuous mesh with identical or different mesh size. This embodiment provides maximum possibility of tissue growing inward without simultaneously preventing the mass movement or peristaltic movement of the intestine.

Figure 5:
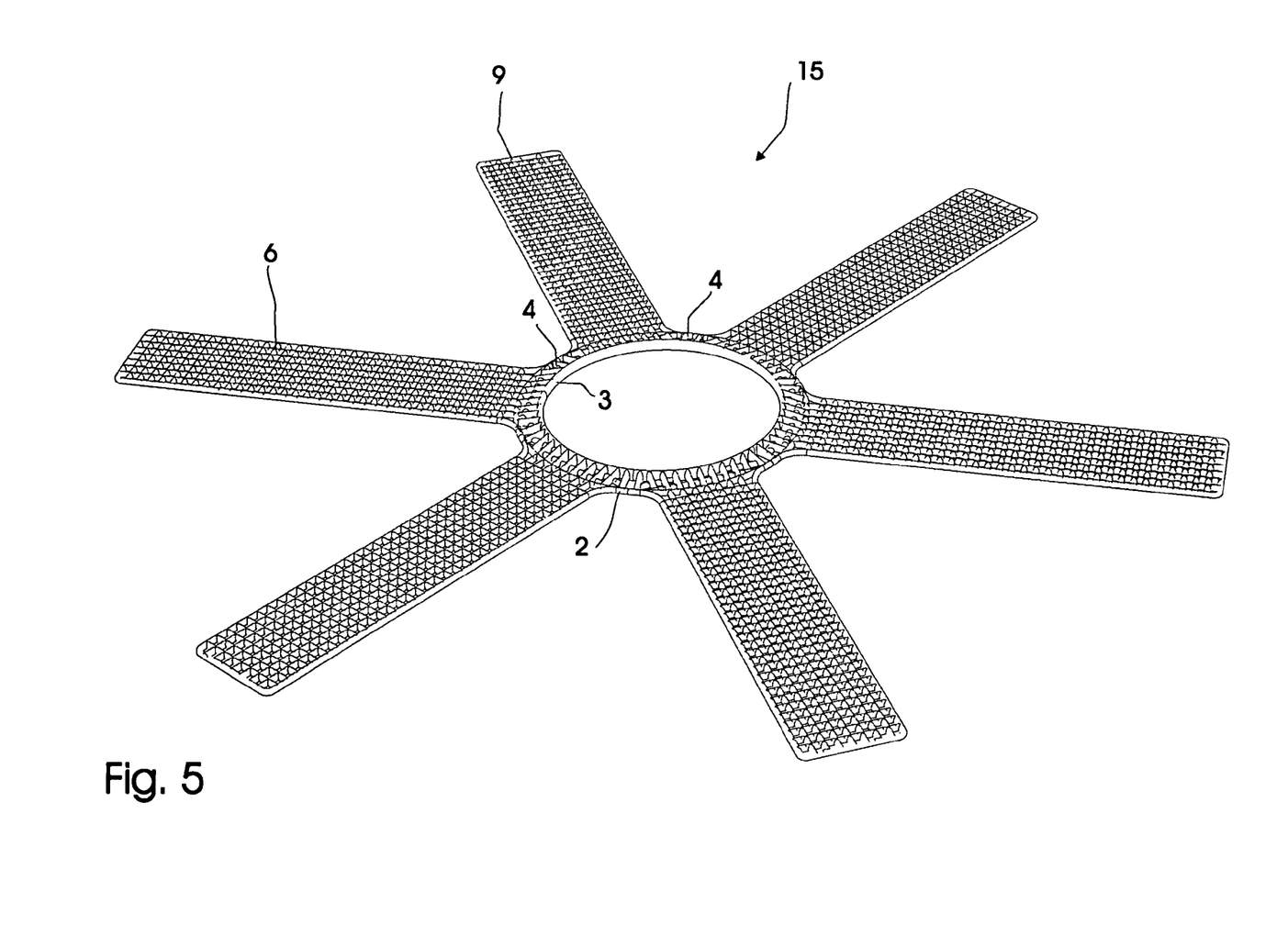
FIG. 5 is a perspective view of a fifth embodiment of an implant for use in the method according to the invention.

FIG. 5 shows a fifth embodiment of the present invention, and like parts are similarly referenced. The fifth embodiment 15 of the implant for use in a method according to the present invention in FIG. 5 is an alternative to the fourth embodiment in FIG. 4. The inner ring 3 has a larger axial thickness than the outer ring 2 and the connecting links 4 connecting the two rings 2,3 are made of strong thread to thereby distribute loads and stresses equally across the entire extent of the rings.

Preferred radial thickness of the rings in the embodiments in FIGS. 1, 2 and 3 are 5 mm, preferably 4 mm, and especially 3 mm.

The thickness of the rings of the embodiments in FIGS. 4 and 5 can be as small as 1 mm and even smaller than 0.5 mm. The axial extent of the rings is typically between 0.5 and 5 mm.

The inside diameter of the inner ring corresponds to or is slightly larger than the outside cross section of the section of intestine which is to be passed through this ring, and the inside diameter of the outer ring is larger than the outside diameter of the inner ring.

Within the scope of the invention it will however be clear to a person skilled in the art that thickness and diameters of rings and connecting links depend on the actual need and such that the flexibility and retaining capability are not compromised.

The meshes have an initial length sufficiently great to be anchored securely, the surgeon being able to shorten the mesh to an accurate and sufficient length.

Other types of anchoring means are also comprised within the scope of the invention, for example one single thread can just as well serve to anchor the implant in the external rectus fascia.

The implant according to the present invention has its preferred application for prophylactic and therapeutic treatment of a hernia originating from an enterostomy. The implant according to the present invention can however be used in other connections. For example an implant can be used for surrounding oesophagus to relieve an oesophagus hernia or preventing such a hernia from developing in a previously identified critical site.

EXAMPLES

The following example illustrate the most preferred embodiments and the tests conducted to confirm their utility.

Pilot Study

Materials

Implants according to the embodiment of FIG. 4 with six anchoring means were obtained from Medic House A/S, Østre Havnevej 31, Svendborg, Denmark. The implants were laser cut from polypropylen mesh sheets. The width of the ring was 2 cm. The distance from the centre of the ring to the free end of the anchoring means was 6 cm.

Patients

A total of 25 patients (15 male) with median age of 71 years (range 39-93) who were scheduled for elective surgery for rectosigmoidal cancer and with a high probability for a permanent end-colostomy, were included in the study. Patients who had inflammatory bowel disease, a known immunodeficiency disease, a mechanical cardiac valve, American Society of Anaesthesiology (ASA) class IV-V or had a short expected survival after surgery were not included in the study. Risk factors for development of parastomal hernia were recorded prior to surgery. All patients were registered with their clinical data, with emphasis on occurrence of surgical risk factors. The body mass index (BMI), smoking habits, presence of chronic obstructive lung disease (COLD), diabetes, ischaemic heart disease and prior occurrence of an abdominal wall hernia were registered before surgery.

Operative Procedure

Initially a first circular incision in the skin (1 cm wide) was made. An implant with an inner diameter approximately ½ cm larger than the colonic diameter was chosen. The mesh was immersed in a GENTAMYCIN® solution (240 mg in 100 mL isotonic saline) before implantation. The first anchoring means was pulled through the first peripheral skin and arranged above the external rectus fascia. Hereafter, the same procedure was repeated for each anchoring means. The central ring was then fixated with four 2-0 Prolene corner sutures to the external rectus fascia and a second cross-formed incision in the external rectus fascia were made. Afterwards the colon was pulled through the central opening of the implant and fixated according to conventional stoma creating procedure with three point sutures. The serosa of the colon was not fixated to the mesh. The duration of the procedure in total was 10-15 minutes.

Post Surgical Procedure

After surgery on the first postoperative day and until the patient was discharged, the stoma was evaluated on a daily basis on regular daily rounds. Any complication related to the mesh or stoma before discharge was registered as an immediate complication. The patient was afterwards seen in the out-patient unit 1, 3, 6, 12, 18 and 24 months after surgery. Here an experienced stoma nurse and a surgeon evaluated if there were any clinical signs of parastomal hernia (defined as a persistent protrusion around the stoma in a supine and/or standing position), inflammatory reaction, signs of infection, signs of fistula formation in the vicinity of the stoma, a foreign body reaction or any signs of stricture formation. These complications were registered as long-term complications. In addition a dynamic abdominal ultrasound (supine position with and without increased intraabdominal pressure) was made 6 and 12 months after surgery to determine if there were any ultrasonographic signs of hernia. If the abdominal ultrasound did not reveal any sign of hernia but there still was a clinical suspicion by a senior surgeon, an abdominal CT-scan was performed.

Results

An experienced stoma nurse and a surgeon evaluated immediate and longterm complications. Abdominal ultrasound was done at 6 and 12 months follow-up. Parastomal hernia was defined as both clinical and ultrasonographic signs of protrusion in the vicinity of the stoma.

tions related to the mesh. In both cases, one of the anchoring means was placed superficially during the primary operation resulting in penetration through the overlaying skin. Both the patients were reoperated through a small skin incision and the length of the anchoring means was shortened and skin was closed. Both the procedures were done electively under local anaesthesia and there were no signs of subcutaneous infection or abscess formation.

In the long term follow up, no patients had bowel strictures, inflammatory reaction, signs of foreign body reaction, infection or fistula formation in the vicinity of the stoma. There were two patients who had both clinical and objective signs of

TABLE 1

Patient demographics.

| Patient no: | Gender | Age | BMI (kg/m$^2$) | Smoking | COLD | IHD | Diabetes | Previous hernia | Prostate problems | Parastomal hernia |
|---|---|---|---|---|---|---|---|---|---|---|
| 1 | M | 74 | 20 | Y | Y | N | N | N | N | N |
| 2 | F | 93 | 20 | N | N | N | N | N | — | N |
| 3 | M | 60 | 31 | N | N | N | N | N | N | N |
| 4 | F | 69 | 20 | Y | N | N | N | N | — | N |
| 5 | F | 72 | 30 | N | Y | N | Y | N | — | N |
| 6 | M | 53 | 28 | Y | N | N | N | N | N | Y |
| 7 | M | 70 | 23 | N | N | N | N | N | N | N |
| 8 | F | 69 | 21 | N | N | Y | N | N | — | N |
| 9 | F | 55 | 28 | N | N | N | N | N | — | N |
| 10 | M | 55 | 28 | N | N | N | N | N | N | N |
| 11 | M | 72 | 30 | N | N | Y | N | N | N | Y |
| 12 | F | 57 | 21 | N | N | N | N | N | — | N |
| 13 | M | 72 | 24 | Y | N | N | N | Groin | N | N |
| 14 | M | 69 | 24 | N | N | N | N | Groin | Y | N |
| 15 | M | 81 | 21 | N | N | N | N | Groin | N | N |
| 16 | F | 74 | 23 | N | N | N | N | N | — | N |
| 17 | M | 76 | 22 | N | N | N | N | Groin | Y | N |
| 18 | F | 72 | 22 | N | N | N | N | N | — | N |
| 19 | M | 79 | 25 | N | N | Y | N | N | Y | N |
| 20 | M | 77 | 23 | N | N | N | N | Groin | | N |
| 21 | M | 75 | 21 | N | N | N | N | Groin | N | N |
| 22 | M | 69 | 28 | N | N | N | N | N | N | N |
| 23 | F | 59 | 23 | Y | N | N | N | N | — | N |
| 24 | F | 39 | 16 | N | N | N | N | N | — | N |

N = no.
Y = yes.
M = male.
F = female.
BMI = body mass index.
COLD = chronic obstructive lung disease.
IHD = ischaemic heart disease.
Prostate problems = defined as clinical signs of hypertrophic prostate.

One patient died on postoperative day 8 because of a postoperative cardiovascular complication. A total of 24 patients were therefore available for follow-up. All operations were elective and all patients were operated for rectosigmoidal neoplasia through a midline laparotomy. The operations were made by 4 surgeons and the frequency of operations per surgeon was 13, 5, 4 and 2 respectively. The median body mass index was 23 (range 16-31). The median time to the first bowel movement was 3 days (1-6 days). The median follow-up time was 12 months (range 2-26).

Four patients had an infection in their midline incision, and were treated by local drainage without the need for further surgery. Two patients had a fascial dehiscence and were reoperated on postoperative day 8 (patient no. 13) and 10 (patient no. 20), respectively. Two patients had pneumonia (patients no. 1 and 2) and two had a urinary tract infection (patients no. 2 and 17) and were treated with systemic antibiotics.

None of the 24 patients had any immediate complications related to the stoma. Two patients had long term complicaparastomal hernia at 6 and 12 month follow-up control, respectively. Both patients did not have any problems with their stoma appliances and the major complaint was aesthetical.

Conclusions

Implantation of a polypropylene mesh in an onlay position seems to be a safe procedure with an apparently low risk of parastomal hernia formation.

Placement of a mesh in a sublay position as in prior art techniques involves extensive dissection under the rectus muscle, superficial to the deep fascia, before placement of the implant mesh and fixation of the implant mesh with the lateral sutures and this will prolong surgery substantially.

In contrast, placement of a mesh in an onlay position would give the advantage of shorter operation time, no muscular dissection and two different operative fields separating the midline incision and the stoma area. In case of hernia formation, a laparoscopic repair in an "untouched" field is possible and thus might be a more advantageous choice.

A surgical procedure through the muscles of the abdominal wall creates a potential site of weakness, in particularly in relation to an enterostomy. Although the abdominal wall muscles should fit around the stoma opening, the muscles could get away from the edges of the stoma in which case a hernia, i.e. an area of the abdominal wall adjacent to the stoma where there is no muscle, is created. In the surgical method according to the present invention a novel implant is inserted surrounding the intestine on top of the fascia to which the implant is secured. Radiating meshes serves for fixation and securing of the implant to the fascia so that the meshes put a pressure on the muscles thereby preventing hernia formation. The implant advantageously reinforces the muscle structure in risk of hernia formation.

What is claimed is:

1. A method for prevention of a parastomal hernia in a patient including the steps of:
    making a first incision in the skin,
    introducing through the first incision an implant comprising a substantially flat ring having a central opening, wherein the implant is provided with a number of anchoring means radiating from an outer circumference of the ring,
    positioning the opening of the ring substantially below the first incision on top of the external rectus fascia,
    directing the number of anchoring means to each of their securing positions on top the fascia and securing the anchoring means to the fascia,
    making a second incision in the external rectus fascia, and
    pulling an end of an intestine to be externalized through the second incision, the central opening of the implant, and the first incision, thus creating a stoma.

2. A method according to claim 1 which further comprises making a third incision in the skin so that each of the number of anchoring means is directed to their securing position on top of the fascia by pulling a free end of each anchoring means through the third incision in the skin.

3. A method according to claim 1 which further comprises mechanically straightening out the anchoring means in the space between the fascia and the skin so that each of the number of anchoring means can be directed to their securing position on top of the fascia.

4. A method according to claim 1 wherein the implant is immersed in an antibiotic prior to implantation.

5. A method according to claim 1 wherein the steps of the method is performed through a laparoscopically procedure.

6. A method according to claim 1 wherein the first incision is a circular incision.

7. A method according to claim 6 wherein the circular incision has a diameter of between 0.5 cm and 2 cm.

8. A method according to claim 1 wherein the second incision is a cross-formed.

9. A method according to claim 1 wherein the ring and the anchoring means are integrated mesh parts.

10. A method according to claim 1 modified in that the step of making a second incision is made subsequent to the step of making a first incision.

11. An apparatus for prevention of a parastomal hernia in a patient comprising an implant comprising a substantially flat ring having a central opening, wherein the implant is provided with a number of anchoring means radiating from an outer circumference of the ring, but not extending into the central opening, with the opening of the ring configured and dimensioned to be positionable on top of the external rectus fascia of the patient, and with the number of anchoring means configured and dimensioned to be securable to the fascia for holding the implant in position on top of the fascia, so that an end of an intestine of the patient can be received in the central opening of the implant to create a stoma.

* * * * *